(12) United States Patent
Jain et al.

(10) Patent No.: US 10,702,520 B1
(45) Date of Patent: Jul. 7, 2020

(54) PHARMACEUTICAL COMPOSITIONS OF POSACONAZOLE

(71) Applicant: SLAYBACK PHARMA LLC, Princeton, NJ (US)

(72) Inventors: Paras P. Jain, Maharashtra (IN); Girish Kumar Jain, Maharashtra (IN)

(73) Assignee: SLAYBACK PHARMA LLC, Princeton, NJ (US)

( * ) Notice: Subject to any disclaimer, the term of this patent is extended or adjusted under 35 U.S.C. 154(b) by 0 days.

(21) Appl. No.: 16/410,149

(22) Filed: May 13, 2019

(30) Foreign Application Priority Data

Jan. 29, 2019 (IN) .............................. 201941003513

(51) Int. Cl.
| | | |
|---|---|---|
| *A61K 31/496* | (2006.01) | |
| *A61K 47/38* | (2006.01) | |
| *A61K 9/20* | (2006.01) | |
| *A61P 31/10* | (2006.01) | |

(52) U.S. Cl.
CPC .......... *A61K 31/496* (2013.01); *A61K 9/2095* (2013.01); *A61K 47/38* (2013.01); *A61P 31/10* (2018.01)

(58) Field of Classification Search
None
See application file for complete search history.

(56) References Cited

U.S. PATENT DOCUMENTS

| | | | |
|---|---|---|---|
| 6,881,745 B2 | 4/2005 | Hayes et al. | |
| 10,022,373 B2 | 7/2018 | Wan et al. | |
| 2011/0034478 A1 | 2/2011 | Fang et al. | |
| 2011/0123627 A1 | 5/2011 | Fang et al. | |
| 2015/0150990 A1 | 6/2015 | Fang et al. | |
| 2015/0231081 A1 | 8/2015 | Kulkarni et al. | |
| 2018/0228798 A1 | 8/2018 | Prathap et al. | |

FOREIGN PATENT DOCUMENTS

| | | |
|---|---|---|
| EP | 3342399 A1 | 7/2018 |
| EP | 3342399 A1 | 7/2018 |
| WO | 1998000113 A1 | 1/1998 |
| WO | WO 98/00113 A1 | 1/1998 |
| WO | 2009129300 A2 | 10/2009 |
| WO | 2009129301 A2 | 10/2009 |
| WO | WO 2009/129300 A2 | 10/2009 |
| WO | WO 2009/129301 A2 | 10/2009 |
| WO | WO 2012/148550 * | 11/2012 |
| WO | WO 2017/025292 A1 | 2/2017 |
| WO | 2017032908 A1 | 3/2017 |
| WO | WO 2017/032908 A1 | 3/2017 |
| WO | WO 2019/240898 A2 | 12/2019 |

OTHER PUBLICATIONS

Ritesh Fule et al., Hot Melt Extruded Amorphous Solid Dispersion of Posaconazole with Improved Bioavailability: Investigating Drug-Polymer Miscibility with Advanced Characterisation, Research Article, Hindawi Publishing Corporation, BioMed Research International, vol. 2014, Article ID 146781, 16 pages, http://dx.doi.org/10.1155/2014/146781, published Jul. 21, 2014.

Fule et al., "Hot Melt Extruded Amorphous Solid Dispersion of Posaconazole with Improved Bioavailabilty: Investigating Drug-Polymer Miscibility with Advanced Characterization," BioMed Research International, vol. 2014, Published Jul. 21, 2014, 16 pages.

International Search Report and Written Opinion of the International Searching Authority dated Oct. 24, 2019, for International Application No. PCT/US2019/031995.

* cited by examiner

*Primary Examiner* — Dennis Heyer

(74) *Attorney, Agent, or Firm* — Birch, Stewart, Kolasch & Birch, LLP

(57) ABSTRACT

Delayed-release pharmaceutical compositions prepared by hot-melt extrusion are provided, where the compositions comprise an azole anti-fungal drug having poor water solubility, an enteric polymer and a non-enteric polymer, and wherein the pharmaceutical composition may be orally administered to a patient in either the fed or fasted state. Preferably, the delayed-release pharmaceutical compositions prepared by hot-melt extrusion comprise posaconazole, HPMC-AS and HPC. Preferably, following oral administration of the pharmaceutical compositions, there is no substantial difference in the pharmacokinetic parameters ($T_{max}$, $C_{max}$, $AUC_{0-t}$ and/or $AUC_{0-infinity}$) of the azole anti-fungal drug, regardless of whether the pharmaceutical compositions are administered to a subject in the fed or fasted state.

19 Claims, 3 Drawing Sheets

PHARMACEUTICAL COMPOSITIONS OF POSACONAZOLE

CROSS-REFERENCE TO RELATED APPLICATIONS

This application claims foreign priority to Indian Application No. IN 201941003513, filed on Jan. 29, 2019, which is incorporated herein by reference in its entirety.

FIELD OF THE INVENTION

The present invention relates to delayed-release pharmaceutical compositions prepared by hot-melt extrusion, comprising an azole anti-fungal drug having poor water solubility, an enteric polymer and a non-enteric polymer, wherein the composition may be administered in either the fed or fasted state. In certain embodiments, the composition is a granulate material that can be filled into a capsule or can be compressed into a tablet.

BACKGROUND OF THE INVENTION

The present invention relates to delayed-release pharmaceutical compositions comprising an azole anti-fungal drug having poor water solubility, wherein the composition may be administered in either the fed or fasted state. Azole anti-fungal drugs having poor water solubility (e.g., including, but not limited to, itraconazole, posaconazole, voriconazole and terconazole) have been developed for treatment and/or prevention of fungal infections, including invasive fungal infections.

Posaconazole is a broad-spectrum triazole antifungal drug marketed under the tradename NOXAFIL® as a solution for injection, oral suspension, and gastro-resistant tablet for the treatment and prophylaxis of invasive fungal infections. NOXAFIL® is indicated for the prophylaxis of invasive *Aspergillus* and *Candida* infections in severely immunocompromised patients, such as hematopoietic stem cell transplant recipients with a graft-versus-host-disease and patients with hematologic malignancies with prolonged neutropenia from chemotherapy. The oral suspension is indicated for the treatment of oropharyngeal candidiasis (OPC) as well.

Posaconazole has the chemical name of 4-[4-[4-[4-[[(3R,5R)-5-(2,4-difluorophenyl)tetrahydro-5-(1H-1,2,4-triazol-1-ylmethyl)-3-furanyl]methoxy]phenyl]-1-piperazinyl]phenyl]-2-[(1S,2S)-1-ethyl-2-hydroxypropyl]-2,4-dihydro-3H-1,2,4-triazol-3-one, and has the structural formula (I):

Posaconazole free base has a solubility of approximately 0.8 mg/mL at gastric pH. However, when posaconazole dissolved in the gastric fluids reaches the environment of the intestines, which is less acidic (typically a pH of about 6.4), a substantial amount of the dissolved posaconazole precipitates, hindering absorption in the intestines. It has been determined that in environments where the pH is about pH 6.4 or higher, the solubility of posaconazole free base is less than about 1 µg/mL.

Bioavailability of posaconazole oral suspension (NOXAFIL®) is significantly enhanced when co-administered with food. For this reason, the oral suspension is administered during or immediately following a full meal to enhance the oral absorption of the drug. A delayed-release tablet formulation which releases posaconazole in the small intestine was developed to maximize systemic absorption and to overcome the food effect limitations of oral suspension formulations of posaconazole. However, commercially available posaconazole delayed-release tablets (NOXAFIL®) are only prescribed for use with food because of relatively poor bioavailability when administered under fasted conditions.

Itraconazole is a triazole antifungal drug used for the treatment of fungal infections, including superficial infections, such as onychomycosis, as well as systemic fungal infections, for example, pulmonary or extrapulmonary blastomycosis, histoplasmosis, and aspergillosis. Itraconazole has solubility of less than 1 µg/mL in water and 6 µg/mL in 0.1 N Hydrochloric acid. Itraconazole has the following structural Formula (II):

Formula (I)

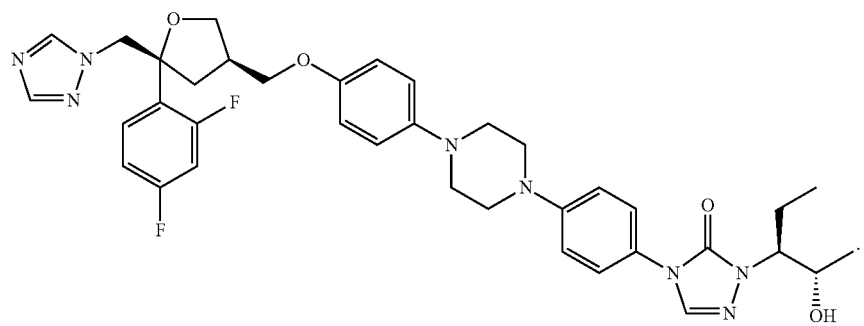

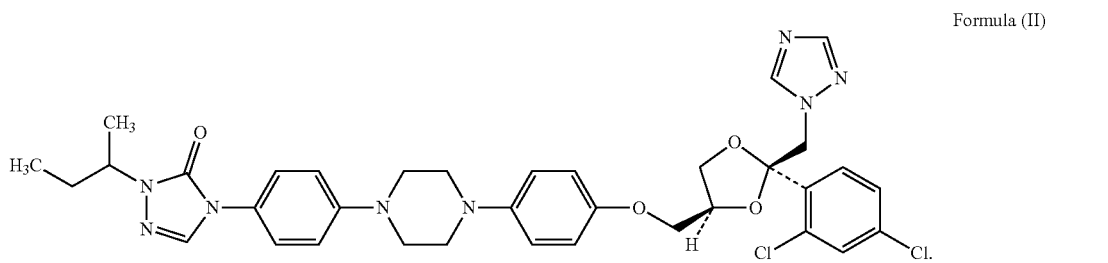 [SMILES: CCC(C)n1ncn(-c2ccc(N3CCN(c4ccc(OC[C@H]5CO[C@](Cn6cncn6)(c6ccc(Cl)cc6Cl)O5)cc4)CC3)cc2)c1=O]

Formula (II)

Commercially available solid oral dosage forms of itraconazole (SPORANOX®, ONMEL® and TOLSURA®) must be taken with food because bioavailability of itraconazole in these formulations is enhanced when administered under fed conditions.

Antifungal prophylaxis recipients routinely include two key populations: (i) patients with acute myelogenous leukaemia (AML), myelodysplastic syndrome (MDS), or other acute haematological malignancies, who may develop neutropenia and chemotherapy-induced side effects, namely, severe nausea or vomiting; and (ii) allogeneic hematopoietic stem cell transplant (HSCT) recipients, who routinely develop graft-versus-host disease (GVHD) and its associated complications, including severe mucositis or diarrhea. Adequate food intake to obtain optimal drug exposure may be difficult for these patients. Hence, there exists a need for improved oral pharmaceutical compositions for azole anti-fungal drugs that have poor water solubility, which also addresses the food effect.

SUMMARY OF THE INVENTION

The present application relates to addressing the food effect, which was problematic with prior formulations. Thus, improved pharmaceutical compositions are provided, which comprise an azole anti-fungal drug having poor water solubility (e.g., including, but not limited to, itraconazole, posaconazole, voriconazole and terconazole) and which exhibit improved bioavailability in the fasting state, compared to the existing formulations.

In certain embodiments, upon oral administration to a patient, the pharmaceutical compositions described herein exhibit less variability in pharmacokinetic parameters ($T_{max}$, $C_{max}$, $AUC_{0-t}$ and/or $AUC_{0-infinity}$) between the fasted and fed states. For example, certain embodiments relate to compositions for oral administration that provide posaconazole to a patient population with lower variability in bioavailability (e.g., a narrower observed range for $C_{max}$ and AUC values), thus providing consistent PK parameters across a patient population to whom the formulation is administered.

Certain aspects relate to compositions for oral administration that provide higher posaconazole bioavailability than commercially available formulations such as NOXAFIL®, e.g., compositions that yield higher plasma levels in a fasted state. In addition, the present application also provides compositions for oral administration that provide an acceptable plasma level of posaconazole when administered to a patient in a fed state.

An aspect of the present invention relates to pharmaceutical compositions comprising an azole anti-fungal drug having poor water solubility, which is suitable for oral administration, wherein the composition may be administered in either the fed or fasted state. In certain aspects, the application describes posaconazole compositions that are suitable for oral administration to patients, and which provide uniform plasma level(s) and sufficient posaconazole exposure (AUC), in fasted and/or fed states. The application also provides posaconazole compositions that exhibit less intra-subject variability and/or less inter-subject variability in pharmacokinetic parameters ($T_{max}$, $C_{max}$, $AUC_{0-t}$ and/or $AUC_{0-infinity}$) than commercially available posaconazole formulations, e.g., NOXAFIL®.

In another embodiment, the invention provides delayed-release pharmaceutical compositions suitable for oral administration comprising azole anti-fungal drugs having poor water solubility, which are prepared by hot-melt extrusion, wherein the composition may be administered to a patient in either the fed or fasted state. Preferably, following oral administration of said pharmaceutical composition to subjects, there is no substantial difference in the pharmacokinetic parameters ($T_{max}$, $C_{max}$, $AUC_{0-t}$ and/or $AUC_{0-infinity}$) of the azole anti-fungal drug having poor water solubility, regardless of whether the pharmaceutical composition is administered to a subject in the fed or fasted state. By "no substantial difference" to meant that the values for the pharmacokinetic parameters ($T_{max}$, $C_{max}$, $AUC_{0-t}$ and/or $AUC_{0-infinity}$) are within about 75-125% of each other.

In yet another embodiment, the invention relates to a delayed-release pharmaceutical composition prepared by hot-melt extrusion suitable for oral administration, the composition comprising an azole anti-fungal drug having poor water solubility, an enteric polymer and a non-enteric polymer, wherein the composition may be orally administered to a patient in the fed and/or fasted state.

In another embodiment, the invention relates to a delayed-release pharmaceutical composition prepared by hot-melt extrusion, suitable for oral administration, the composition comprising an azole anti-fungal drug having poor water solubility, hydroxypropylmethyl cellulose acetate succinate (HPMC-AS) and hydroxypropyl cellulose (HPC), wherein the composition may be administered in the fed and/or fasted state.

Another aspect of the invention relates to pharmaceutical compositions comprising an azole anti-fungal drug having poor water solubility, which is suitable for oral administration, which exhibit less variability in pharmacokinetic parameters than the commercially available formulations.

Yet another aspect of the invention relates to pharmaceutical compositions comprising an azole anti-fungal drug having poor water solubility, which is suitable for oral administration, having improved bioavailability in the fasting state than the commercially available formulations.

In an embodiment, the invention provides delayed-release pharmaceutical compositions suitable for oral administration, comprising an azole anti-fungal drug having poor water solubility, which is prepared by hot-melt extrusion, wherein the composition exhibits less variability in pharmacokinetic parameters than the commercially available formulations.

In another embodiment, the invention provides delayed-release pharmaceutical compositions comprising posaconazole prepared by hot-melt extrusion for oral administration, wherein the composition provides an improved bioavailability in fasting state than the commercially available posaconazole formulations (NOXAFIL®).

Yet another aspect of the invention relates to pharmaceutical compositions of posaconazole comprising (i) an extrudate comprising posaconazole, an enteric polymer and a non-enteric polymer and (ii) an extra-granular fraction comprising an enteric polymer and a non-enteric polymer, wherein the composition may be administered in the fed and/or fasted state.

An aspect of the invention also relates to stable pharmaceutical compositions of posaconazole comprising (i) an extrudate comprising posaconazole, an enteric polymer and a non-enteric polymer and (ii) an extra-granular fraction comprising an enteric polymer and a non-enteric polymer, wherein the composition may be administered in the fed and/or fasted state.

In an embodiment, the invention provides delayed-release pharmaceutical compositions of posaconazole prepared by hot-melt extrusion for oral administration comprising (i) an extrudate comprising posaconazole, an enteric polymer and a non-enteric polymer and (ii) an extra-granular fraction comprising an enteric polymer and a non-enteric polymer, wherein the composition may be administered in the fed and/or fasted state.

Yet another embodiment provides stable delayed-release pharmaceutical compositions of posaconazole prepared by hot-melt extrusion for oral administration comprising (i) an extrudate comprising posaconazole, an enteric polymer and a non-enteric polymer and (ii) an extra-granular fraction comprising enteric polymer and a non-enteric polymer, wherein the composition may be administered in the fed and/or fasted state.

In an embodiment, the invention provides delayed-release pharmaceutical compositions of posaconazole prepared by hot-melt extrusion for oral administration comprising (i) an extrudate comprising posaconazole, hydroxypropylmethyl cellulose acetate succinate and hydroxypropyl cellulose and (ii) an extra-granular fraction comprising hydroxypropylmethyl cellulose acetate succinate and hydroxypropyl cellulose, wherein the composition may be administered in either the fed or fasted state.

Yet another embodiment provides stable delayed-release pharmaceutical compositions of posaconazole prepared by hot-melt extrusion for oral administration comprising (i) an extrudate comprising posaconazole, hydroxypropylmethyl cellulose acetate succinate and hydroxypropyl cellulose and (ii) an extra-granular fraction comprising hydroxypropylmethyl cellulose acetate succinate and hydroxypropyl cellulose, wherein the composition may be administered in either the fed or fasted state.

In yet another embodiment, the present invention provides a method for treatment or prevention of fungal infection, which method comprises administering to a human in fasted state, a solid oral dosage form comprising an amount of posaconazole effective to treat or prevent said fungal infection, wherein the area under the serum concentration versus time curve ($AUC_{0-inf}$) of the posaconazole in the human subsequent to said administering is from 75% to 125% of the mean area under the posaconazole serum concentration versus time curve ($AUC_{0-inf}$) resulting from administration of control posaconazole delayed release oral tablets containing the same amount of posaconazole to a cohort of humans in a fed state.

In one embodiment, the present invention provides a method for treatment or prevention of fungal infection, which method comprises
a) providing a pharmaceutical composition of posaconazole as described in the present specification to a human without regards to food, e.g., wherein the pharmaceutical compositions do not have a food effect; and
b) administering said pharmaceutical composition to a human, in need thereof, without regards to food.

DETAILED DESCRIPTION OF THE INVENTION

Figure 1:
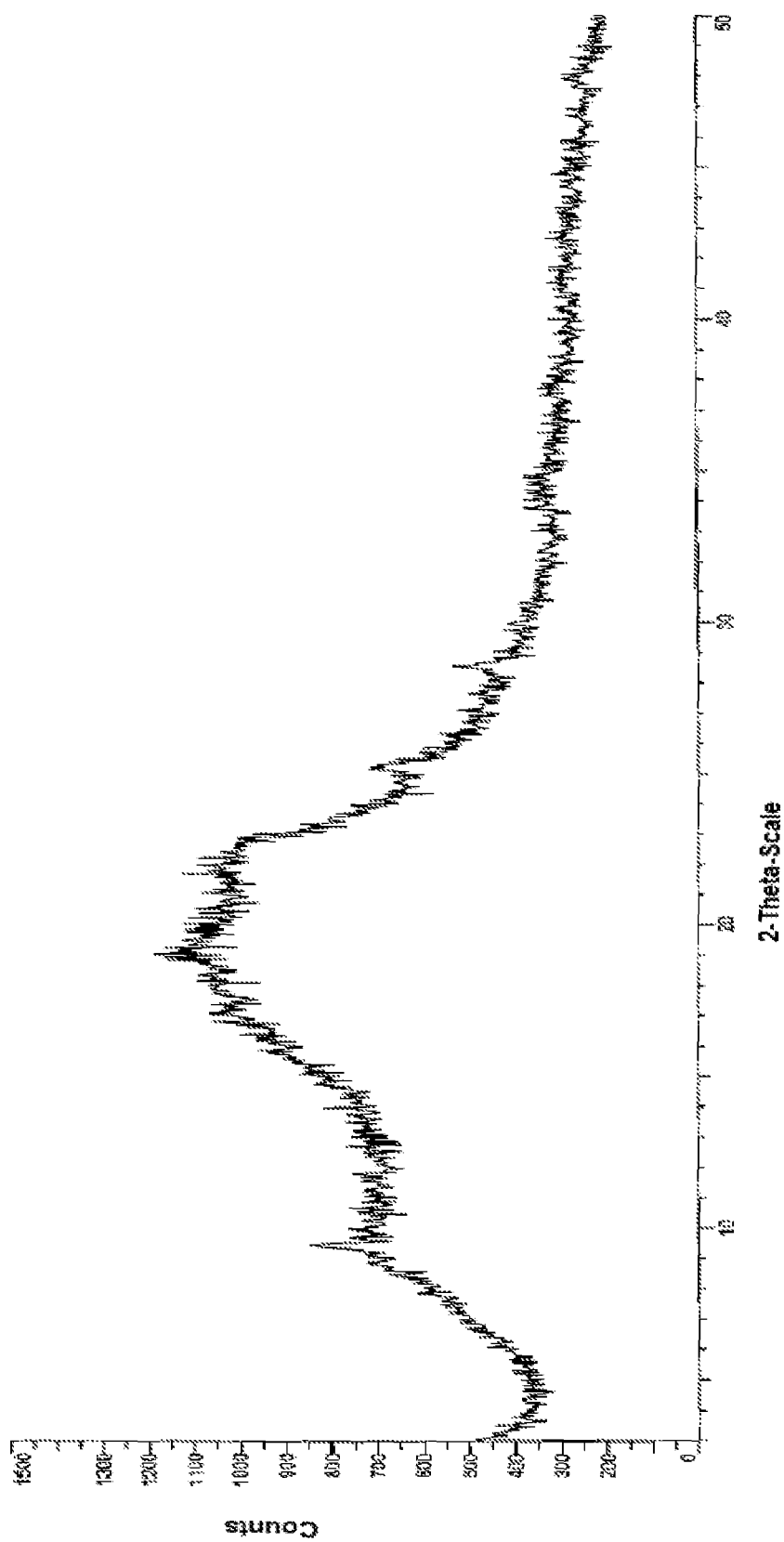
FIG. 1 Illustrate X-ray powder diffraction pattern of extrudate granules obtained in Example 1.

Unless defined otherwise, all the technical and scientific terms used herein have the same meanings as commonly known by a person skilled in the art. In the case that there is a plurality of definitions for the terms herein, the definitions provided herein will prevail.

The term "pharmaceutically acceptable substances" includes those, which, according to a common medical judgment, are suitable to be in contact with a tissue of a patient without any inappropriate toxicity, irritation, allergic response, etc., have a reasonable balance between advantages and disadvantages, and can be applied to its target use effectively.

The terms "pharmaceutical composition", "pharmaceutical product", "pharmaceutical dosage form", "dosage form", "pharmaceutical formulation", etc., refer to a pharmaceutical composition administered to a patient in need of treatment, which is typically in the form of a powder, a granule, a pill, a capsule, a tablet, a solution, a suspension, or a patch, etc.

The term "bioavailability" indicates the extent to which a drug or another substance is utilized by a target tissue after administration.

The term "in vivo" in general means in the living body of a plant or animal, whereas the term "in vitro" generally means outside the body and in an artificial environment.

The term "peak time of plasma drug concentration ($T_{max}$)" means the time when peak plasma drug concentration ($C_{max}$) is attained after drug administration.

The term "peak plasma drug concentration ($C_{max}$)" means the maximum plasma drug concentration attained after drug administration.

The term "$AUC_{0-infin}$," means the area under a plasma drug concentration—time curve from time point of 0 to infinity after drug administration, and the term "$AUC_{0-t}$" means the area under a plasma drug concentration—time curve from time point of 0 to t after drug administration.

As used herein, the term "improved bioavailability" refers to the increase in concentration of a drug in the body fluid provided by the compositions of the present invention as compared to the concentration of the drug in the body fluid from the reference formulation under identical conditions.

The term "extrudate" as used herein refers to solid solutions, solid dispersions, molecular dispersions and glass solutions of posaconazole with one or more polymers and optionally including other pharmaceutically acceptable excipients.

As used herein the term "enteric polymer" is a polymer that is substantially Insoluble and/or impermeable to the acidic environment of the stomach (e.g., at a pH of about 4.5 or less) and soluble or permeable in the environment of the intestine (pH of about 5-7).

As used herein, the term "stable" is defined as no more than about 5% loss of posaconazole under typical commercial storage conditions. In certain embodiments, the formulations of the present invention will have no more than about 3% loss of posaconazole, more preferably, no more than about 2% loss of posaconazole, under typical commercial storage conditions. The composition retains at least about 95% of the potency of posaconazole after storing the composition at 40° C. and 75% relative humidity for at least three months.

Reference throughout this specification will be made to the administration of a pharmaceutical composition under fed or fasted conditions. It is well understood in the art that the pharmacokinetic performance of some compositions is affected by the presence or absence of food in the gastrointestinal system. These references thus relate to the normally accepted administration circumstances that are referred to in the art as "fed" or "fasted."

As used herein, the term "fasted state" means that the human or other mammal has not ingested 500 calories or more than 500 calories for at least two hours before taking the posaconazole solid oral dosage form and for at least two hours after taking the posaconazole solid oral dosage form.

As used herein, the term "fed state" refers to a human who has eaten a United States Food and Drug Administration (FDA) standard high fat breakfast (or other meal containing a comparable quantity of fat and calories) within said time period. The meal is high in both fat (approximately 50% of total calorie content of the meal) and calories (approximately 800-1000 calories).

The term hot-melt extrusion or hot-melt extruded is used herein to describe a process whereby a composition is heated and/or compressed to a molten (or softened) state and subsequently forced through an orifice in a die where the extruded product is formed into its final shape in which it solidifies upon cooling. The blend is conveyed through one or more heating zones typically by a screw mechanism. The screw or screws are rotated by a variable speed motor inside a cylindrical barrel where only a small gap exists between the outside diameter of the screw and the inside diameter of the barrel. In this conformation, high shear is created at the barrel wall and between the screw fights by which the various components of the powder blend are well mixed and disaggregated. The die can be a dual manifold, multi-manifold or feed-block style die. As used herein, the term extrudate refers to hot-melt extruded composition.

Unless specified otherwise, all the percentages, portions and ratios in the present invention are on weight basis.

Azole anti-fungal drugs having poor water solubility of the present invention include both imidazole anti-fungal drugs and triazole anti-fungal drugs. Examples of azole anti-fungal drugs include but are not limited to clotrimazole, econazole, miconazole, fluconazole, ketoconazole, itraconazole, terconazole, voriconazole, and posaconazole. In a preferred embodiment, the azole anti-fungal drug is posaconazole.

As used herein the term "posaconazole" refers to posaconazole free base or a pharmaceutically acceptable salt, solvate and hydrate thereof. In principle, any crystalline form of posaconazole as well as the amorphous form may be used for the preparation of the pharmaceutical composition of the present invention. In a preferred embodiment, posaconazole amorphous form is used.

Posaconazole has a melting point of 170-172° C., but it degrades at temperatures above 160° C. Hence, the hot-melt extrusion used for the preparation of the pharmaceutical composition of the present invention is conducted at temperatures below 160° C. The hot-melt extrusion may be conducted at a temperature of 40-160° C., preferably at a temperature of 120-150° C. The hot-melt extrusion has to be carried out at a temperature that allows the dissolution of the posaconazole used as staring material within the mixture of enteric polymer and non-enteric polymer.

The pharmaceutical composition according to the invention improves the absorption behaviour of posaconazole in human body, and increases the absorption and bioavailability of the drug in comparison to the both commercially available posaconazole oral formulations (NOXAFIL®). Further, the pharmaceutical composition according to the invention is prepared by a hot melt extrusion process, which is simple and easy to operate, and decreases energy consumption, and increases productivity.

In addition, when preparing the pharmaceutical composition using the hot melt extrusion process according to the invention, the addition of non-enteric polymer lowers the glass transition temperature (Tg) of the pharmaceutical composition, significantly decreasing the torque of the extruder, reducing energy consumption, and increasing productivity.

Specifically, the inventors have found that a composition comprising posaconazole dissolved or dispersed in a carrier material comprising an enteric polymer and a non-enteric polymer at a certain ratio, can increase the solubility of posaconazole in gastrointestinal tract, and can ameliorate the problem of precipitation or crystallization, thereby increasing the absorption of posaconazole in vivo and bioavailability thereof. In another aspect, the composition can also alter the absorption of posaconazole in vivo, increasing $C_{max}$ and AUC without prolonging $T_{max}$ in fasted state. The composition also has better properties in terms of production process, such as good grindability and compressibility.

The carrier material comprises one or more enteric polymers selected from the group consisting of cellulose acetate phthalate, cellulose acetate trimellitate, cellulose acetate succinate, methyl cellulose phthalate, ethylhydroxymethylcellulose phthalate, hydroxypropylmethylcellulose phthalate (HPMC-P), hydroxypropylmethyl cellulose acetate succinate (HPMC-AS), hydroxypropylmethyl cellulose acetate maleate, hydroxypropylmethylcellulose trimellitate, carboxymethylethyl cellulose, polyvinyl butyrate phthalate, polyvinyl acetate phthalate, a methacrylic acid/ethyl acrylate copolymer and a methacrylic acid/methyl methacrylate copolymer, preferably selected from the group consisting of HPMC-P, HPMC-AS, hydroxypropylmethyl cellulose acetate maleate and hydroxypropylmethylcellulose trimellitate, and more preferably is HPMC-AS.

HPMC-AS is commercially available. For example, the AQOAT series of polymers available from Shin-Etsu, provide HPMC-AS polymers in different grades, for example, L, M, and H grades. HPMC-AS polymers have solubility varying from pH5.5 to 6.8. Specifically, grade L is soluble at pH5.5, grade M is soluble at pH6, and grade H is soluble at pH6.8.

Both granular (type G) and micronized (type F) forms of AQOAT HPMC-AS are available, and either would be suitable for use in the present invention. In some embodiments, it is preferred to prepare a composition of the invention using AQOAT HPMCAS grade L wherein the acetyl content is stated to be in the range of 7% to 11% and the range of succinoyl content is stated to be in the range of 10% to 14%. In some embodiments, it is preferred to prepare a composition of the invention using AQOAT HPMC-AS grade M wherein the acetyl content is stated to be in the range of 5% to 9% and the range of succinoyl content is stated to be in the range of 14% to 18%. As used herein, the terms "grade L" and "grade M" refer to grades of HPMCAS that are consistent with the AQOAT line of HPMC-AS grade L and HPMCAS grade M available from Shin-Etsu.

In one embodiment, the weight ratio of posaconazole to enteric polymer is from 1:1 to 1:8, preferably from 1:2 to 1:5, and more preferably 1:3 to 1:4.

The carrier material further comprises a non-enteric polymer which is preferably selected from hydroxypropylmethyl cellulose (hypromellose), hydroxypropyl cellulose (HPC), hydroxyethyl cellulose, polyvinylpyrrolidone (povidone), poly(vinylpyrrolidone/vinylacetate) (copovidone), polyvinylcaprolactam/polyvinylacetate/polyethylene glycol graft copolymer, polyethylene glycol/polyvinyl alcohol graft copolymer, polyethylene oxide, polypropylene oxide, copolymers of ethylene oxide and propylene oxide, polyvinyl alcohol, partially saponified polyvinylalcohol, macrogolglycerol hydroxystearate, polyethylene glycol, and maltodextrins.

Typically, the extrudate contains the enteric polymer and the non-enteric polymer in a weight ratio of 1:1 to 20:1, preferably 10:1 to 18:1 and more preferred from 13:1 to 16:1. Furthermore, the weight ratio of posaconazole to total polymer content of the extrudate is from 1:1 to 1:10, preferably from 1:2 to 1:7, and more preferably 1:3 to 1:5.

According to a preferred embodiment of the present invention, posaconazole is dissolved in or dispersed at a molecular level in a carrier material, wherein the carrier material comprises HPMC-AS as enteric polymer and HPC as non-enteric polymer.

In an embodiment of the present inventions, the extrudate contains about 20-25% (w/w) of posaconazole, about 65-75% of HPMC-AS and about 1-10% (w/w) of HPC.

Accordingly, in some embodiments employing HPMC-AS as an enteric polymer and HPC as non-enteric polymer, it is preferred to prepare a composition comprising posaconazole by a process comprising: (i) dry-blending a mixture of posaconazole, HPMC-AS and HPC, wherein, posaconazole is provided as a particulate material having a particle size of from about 1 micron to about 1 millimetre, thereby forming an intimate mixture of polymers and posaconazole; (ii) heating the mixture to a temperature above the glass transition temperature (Tg) of the HPMC-AS and HPC polymers employed and below the melting point of posaconazole (about 170° C.) and optionally blending the heated mixture, thereby forming a molten dispersion of the posaconazole dissolved in HPMC-AS and HPC; and (iii) cooling the dispersion formed in step (ii) to provide a composition of posaconazole in HPMC-AS and HPC. In some embodiments, optionally after Step (ii), the dispersion formed is extruded prior to carrying out cooling Step (iii). As mentioned herein, other polymers in which posaconazole is soluble and which having similar melting behavior may be used instead of or in addition to HPMC-AS and/or HPC polymers and still be within the scope of the present invention.

The inventors have surprisingly found that by using this process, a pharmaceutical composition can be prepared at a significantly lower temperature, and consequently using considerably less heat energy to prepare the composition, than would be employed by first melting a suitable polymer and then mixing the other constituents of the composition into the molten polymer constituent. Moreover, because posaconazole present in the admixture apparently acts as a fluxing agent promoting polymer melting, the time that the constituents of the composition must remain at temperature to provide a uniform composition can be minimized. The ability to minimize heat energy, temperature of the melt, and the amount of time the melt must be held at temperature to insure homogeneity translates to a surprising reduction in the amount of API that is degraded during formation of a composition of the invention. In keeping with the foregoing discussion of preparatory processes, a melt can be prepared in any convenient apparatus in which an admixture of posaconazole and polymers can be heated and optionally stirred. Solidification can be carried out by merely cooling the melt by any means convenient and in any container convenient. Once a solid is obtained, the solid can be further mechanically processed to provide a convenient form for incorporation into a medicament, for example, tablets or capsules.

It will be appreciated that other methods of preparing a melt, solidifying it, and forming the solid into conveniently sized particles can be utilized without departing from the scope of the invention. For example, conveniently, compositions of the invention may be prepared using an extruder. When an extruder is employed to prepare compositions of the invention, conveniently, the material may be introduced into the extruder either in a pre-flux state, that is, as a dry admixture, or in a fluxed state, that is in a melted, plastic, or semi-solid state achieved after the application of sufficient heat to the admixture to cause the API to dissolve in the polymer, optionally when a fluxed charge is prepared, blending may be employed during heating to promote uniformity of the fluxed material.

If the material is introduced to the extruder in a fluxed state, residence time in the extruder is selected to be just sufficient to insure homogeneity of the composition and the temperature is preferably maintained in the extruder at a level just sufficient to ensure that the material maintains its plasticity so that it can be extruded into a conveniently shaped extrudate. If the material is introduced into an extruder in a pre-flux state, the extruder components, for example, the barrels and any mixing chamber present in the equipment, will be maintained at a temperature sufficient to promote fluxing of the admixture. Temperatures selected for use in processing a composition will also take into account that blending which occurs within the extruder equipment, for example, in a mixing section of the barrels, will also contribute to localized fluxing of the admixture by imparting shear-stresses that induce heating in the mixture. Additionally, it will be appreciated that equipment temperatures and residence times will be selected to minimize the amount of time that the admixture placed into the extruder spends under conditions of heating and/or shear stress so as to minimize the amount of API which is decomposed during formation of the composition, as discussed above.

The process of hot melt extrusion is carried out in the conventional extruders as known to a person skilled in the art. Typically, the melt-extrusion process comprises the steps of preparing a homogeneous melt of one or more drugs, the polymer and the excipients, and cooling the melt until it solidifies.

Melting usually involves heating above the softening point of the polymer. The preparation of the melt can take place in a variety of ways. The mixing of the components can take place before, during or after the formation of the melt. Usually, the melt temperature is in the range of about 50° C. to about 200° C.

Suitable extruders include single screw extruders, intermeshing screw extruders or else multi-screw extruders, preferably twin-screw extruders, which can be co-rotating or counter-rotating and, optionally, be equipped with kneading disks. The extrudates can be in the form of beads, granulates, tubes, needles, bars, strands or cylinders and these can be further processed into any desired shape. If desired, the extrudate can be further processed, for example by milling, to provide a particulate form of the composition.

An aspect of the invention provides a dosage form comprising a composition comprising posaconazole free base dissolved in, or molecularly dispersed in a carrier material comprising HPMC-AS as enteric polymer and hydroxypropyl cellulose as non-enteric polymer. In some embodiments it is preferred to directly incorporate the composition as prepared into a dosage form, for example, placing an extruded shape or a particulate from of a composition of the invention into a capsule without any additional excipients. In some embodiments, it is preferred to directly extrude the molten dispersion into a capsule without additional excipients to provide a dosage form comprising the composition of the invention.

In some embodiments it is preferred to mill a solid form of the composition, for example, milling an extrudate form of the composition, to provide a particulate form of the composition. In some embodiments it is preferred to provide the composition in a granular form. In some embodiments it is preferred to mix the milled particulate form or a granular form of the composition of the invention with one or more extra-granular excipients and press the mixture into a tablet dosage form or charge the mixture into capsules.

The milled extrudate particles may be in crystalline form or amorphous form. In one embodiment, the milled particles of extrudate comprising posaconazole, HPMC-AS and HPC, is in amorphous form as determined by X-ray powder diffraction pattern.

In some embodiments, the extrude may further comprise other pharmaceutically acceptable excipients include, but are not limited to, plasticizers and anti-oxidants. The pharmaceutical composition of the present invention is preferably a granulate/particulate material. The granules/particles may be filled into a capsule or compressed into a tablet. The tablet, which is prepared by compressing the granules/particulates of the present invention, may optionally be coated with an additional enteric polymer or an immediate-release coating.

Moreover, the extrudates/granules of posaconazole of the present invention may be formulated into any suitable dosage form, including but not limited to oral solutions, suspensions, tablets, capsules, delayed release formulations, controlled release formulations, extended release formulations, pulsatile release formulations, and mixed immediate and controlled release formulations.

Other pharmaceutically acceptable excipients may include, but are not limited to, plasticizers, disintegrating agents, lubricants, glidants, diluents, binders, chelating agents, coating agents and the like or mixtures thereof. These pharmaceutically acceptable excipients may be used as intra-granular or extra-granular agents. In one embodiment, enteric and non-enteric polymers used in the present invention are included in intra-granular as well as extra-granular portions.

Suitable enteric polymers as extra-granular agents include cellulose acetate phthalate, cellulose acetate trimellitate, cellulose acetate succinate, methyl cellulose phthalate, ethylhydroxymethylcellulose phthalate, hydroxypropylmethylcellulose phthalate (HPMC-P), hydroxypropylmethyl cellulose acetate succinate (HPMC-AS), hydroxypropylmethyl cellulose acetate maleate, hydroxypropylmethylcellulose trimellitate, carboxymethylethyl cellulose, polyvinyl butyrate phthalate, polyvinyl acetate phthalate, a methacrylic acid/ethyl acrylate copolymer and a methacrylic acid/methyl methacrylate copolymer, preferably selected from the group consisting of HPMCP, HPMCAS, hydroxypropylmethyl cellulose acetate maleate and hydroxypropylmethylcellulose trimellitate, and more preferably is HPMCAS. The enteric polymers may be present in extra-granular portion in an amount of from about 0.5 to 20% w/w of the composition.

Suitable non-enteric polymers as extra-granular agents include hydroxypropylmethyl cellulose, hydroxypropyl cellulose, hydroxyethyl cellulose, polyvinylpyrrolidone (povidone), poly(vinylpyrrolidone/vinylacetate) (copovidone), polyvinylcaprolactam/polyvinylacetate/polyethylene glycol graft copolymer, polyethylene glycol/polyvinyl alcohol graft copolymer, polyethylene oxide, polypropylene oxide, copolymers of ethylene oxide and propylene oxide, polyvinyl alcohol, partially saponified polyvinylalcohol, macrogolglycerol hydroxystearate, polyethylene glycol, and maltodextrins. The non-enteric polymers may be present in extra-granular portion in an amount of from about 0.5 to 20% w/w of the composition.

Suitable diluents or bulking agents which may be used in the pharmaceutical composition of the present invention, include, but are not limited to microcrystalline cellulose, silicified microcrystalline cellulose, lactose, calcium phosphate, starch, dicalcium phosphate, sorbitol/mannitol, sucrose/methyl dextrins, saccharides, including monosaccharides, disaccharides, polysaccharides and sugar alcohols such as arabinose, lactose, dextrose, sucrose, fructose, maltose, mannitol, erythritol, sorbitol, xylitol, lactitol, and the like or mixtures thereof. The diluents may be present in an amount of from about 0.5 to 20% w/w of the composition.

Suitable binders may include, one or more of, but not limited to polyvinyl pyrrolidone (also known as povidone), polyethylene glycol, acacia, alginic acid, agar, calcium carrageenan, cellulose derivative such as ethyl cellulose, methyl cellulose, hydroxypropylmethyl cellulose or sodium carboxymethylcellulose, microcrystalline cellulose, dextrin, gelatin, gum arabic, guar gum, sodium alginate, copovidone, starches, and the like or any other pharmaceutically acceptable substances with cohesive properties, or any combination thereof. The binders may be present in an amount of from about 0.5 to 20% w/w of the composition.

Suitable disintegrating agents which may be used in the pharmaceutical composition of the present invention, include, but are not limited to hydroxyl propyl cellulose, sodium carboxy methyl cellulose, carboxy methyl cellulose, calcium carboxy methyl cellulose, croscarmellose sodium, crospovidone, sodium starch glycolate, corn starch, carboxymethyl starch, hydroxypropyl starch, potato starch, maize starch, alginic acid or a salt, modified starches, calcium silicates, low substituted hydroxypropyl cellulose and the like or mixtures thereof. The disintegrating agents may be present in an amount of from about 0.5 to 20% w/w of the composition.

Plasticizers reduce the viscosity of the polymer melt and thereby allow for lower processing temperature and extruder torque during hot melt extrusion. They further decrease the glass transition temperature of the polymer. Plasticizers which may be used in the pharmaceutical composition of the present invention, include, but are not limited to propylene glycol, polysorbates such as sorbitan monolaurate (Span 20), sorbitan monopalmitate, sorbitan monostearate, sorbitan monoisostearate; citrate ester type plasticizers like triethyl citrate, citrate phthalate; propylene glycol; glycerine; polyethylene glycol (low and high molecular weight); triacetin; dibutyl sebacate, tributyl sebacate; dibutyltartrate, dibutyl phthalate, glycerol palmitosterate and the like or mixtures thereof. The plasticizers may be present in an amount of from about 5 to 20% of polymer in the composition.

Suitable lubricants, anti-adherents and glidants which may be used in the pharmaceutical composition of the present invention, include, but are not limited to, stearic acid and pharmaceutically acceptable salts or esters thereof (for example, magnesium stearate, calcium stearate, sodium stearyl fumarate or other metallic stearate), talc, waxes (for example, microcrystalline waxes) and glycerides, light mineral oil, PEG, silica acid or a derivative or salt thereof (for example, silicates, silicon dioxide, colloidal silicon dioxide and polymers thereof, crospovidone, magnesium aluminosilicate and/or magnesium alumino metasilicate), sucrose ester of fatty acids, hydrogenated vegetable oils (for example, hydrogenated castor oil), and the like or mixtures thereof. The lubricants and glidants may be present in an amount of from about 0.05 to 5% w/w.

The pharmaceutical composition optionally may also comprise an antioxidant. Preferably, the antioxidant is contained in the mixture comprising posaconazole, the enteric polymer and the non-enteric polymer. Examples of antioxidants include butylated hydroxytoluene (BHT), butylated hydroxyanisole (BHA), sodium or potassium metabisulfite, sodium bisulfite, sodium sulfite, sodium thiosulfate, cysteine, acetyl cysteine, methionine, glutathione, sodium formaldehyde sulfoxylate, ascorbic acid and its derivatives like sodium ascorbate, ascorbyl palmitate, tocopherol and its derivatives, tocopheryl succinate, tocopheryl polyethylene glycol succinate (TPGS), and propyl gallate. Typically, the antioxidant is present in the composition in an amount of 0.001-2 wt.-%, preferably 0.01-1 wt.-%.

Suitable chelating agents include, one or more of, but not limited to ethylenediaminetetraacetic acid (EDTA), disodium EDTA and derivatives thereof, niacinamide and derivatives thereof, and sodium desoxycholate and the like or mixtures thereof.

The pharmaceutical composition, may also optionally be coated, e.g., seal coated and/or enteric coated and/or film coated. Preferably, the pharmaceutical composition may be seal coated and finally film coated or it may be seal coated and further enteric coated. Optionally, pharmaceutical compositions of the invention may be film coated. Preferably, the film coating polymer may be present in an amount from about 2 to 10% w/w.

In one embodiment, pharmaceutical compositions of the invention are film coated with Opadry II Yellow available commercially.

In embodiments, it is preferred to prepare posaconazole compositions to release less than about 10% of dissolved or dispersed posaconazole within one hour when the composition is maintained in an environment (pH 1.2 or pH 2.1) and releases more than about 20% of the dissolved or dispersed posaconazole when maintained in an environment equal to a pH from about pH 6.0 to about pH 7.0. In some embodiments it is preferred to measure the posaconazole dissolution profile by placing the composition in a dissolution medium comprising an aqueous HCl solution contained in a paddle dissolution apparatus which has a pH of about pH 1.2 or pH 2.1, and stir the mixture for a first period of stirring lasting about 60 minutes at a paddle speed of 100 RPM while extracting aliquots of the dissolution medium and analyzing them for dissolved posaconazole. In determinations carried out using this method, is it preferred to raise the pH of the dissolution medium at the end of the first period of stirring by adding a mixture of monobasic sodium phosphate and dibasic sodium phosphate salts ($Na_2HPO_4$ and $NaH_2PO_4$) in sufficient quantity to produce a dissolution medium having a pH of from about 6.4 to about 6.8 and continue the stirring while extracting and analyzing aliquots of the dissolution solvent for dissolved or dispersed posaconazole. In some embodiments it is preferred to carry out dissolution tests using a USP dissolution apparatus II (paddle dissolution apparatus) in conjunction with the above-described procedure.

The invention provides methods of prophylactically or therapeutically treating fungal infections by administering a quantity of: a composition of the invention; formulation comprising a composition of the invention or dosage form comprising a composition of the invention, which administered quantity provides from about 50 mg to about 500 mg of posaconazole per day, either in a single or divided dose. In some embodiments it is preferred to administer daily, in either a single or divided dose an amount of: a composition of the invention or dosage form comprising a composition of the invention which provides from about 50 mg to about 400 mg of posaconazole, preferably at least about 100 mg of posaconazole. In some embodiments it is preferred to provide treatment by administering from about 100 mg of posaconazole to about 300 mg of posaconazole per day.

The present invention provides a method for treatment or prevention of fungal infection, which method comprises administering to a human in a fasted state, a solid oral dosage form comprising an amount of posaconazole effective to treat or prevent said fungal infection, wherein the area under the serum concentration versus time curve ($AUC_{0-inf}$) of the posaconazole in the human subsequent to said administering is from 75% to 125% of the mean area under the posaconazole serum concentration versus time curve ($AUC_{0-inf}$) resulting from administration of a control posaconazole delayed release oral tablets containing the same amount of posaconazole to a cohort of humans in a fed state.

Yet another aspect of the invention relates to pharmaceutical compositions comprising an azole anti-fungal drug having poor water solubility, which is suitable for oral administration, having improved bioavailability in fasting state than the commercially available formulation.

In an embodiment, the invention provides delayed-release pharmaceutical compositions comprising an azole anti-fungal drug having poor water solubility, which is prepared by hot-melt extrusion suitable for oral administration, wherein the composition exhibits less variability in pharmacokinetic parameters than the commercially available formulation. Thus, embodiments disclosed herein include at least:

An embodiment that relates to a delayed-release pharmaceutical compositions comprising an azole anti-fungal drug having poor water solubility, which is molecularly dispersed in a mixture of an enteric polymer and a non-enteric polymer; wherein the pharmaceutical composition is prepared by hot-melt extrusion; and wherein the pharmaceutical composition may be administered to a patient in either the fed or fasted state.

Another embodiment relates to delayed-release pharmaceutical compositions, wherein the pharmaceutical composition is prepared by hot-melt extrusion, comprising: the azole anti-fungal drug molecularly dispersed in a mixture of hydroxypropylmethyl cellulose acetate succinate (HPMC-AS); and hydroxypropyl cellulose (HPC); and an extra-granular material comprising an enteric polymer and a non-enteric polymer.

In another embodiment, a delayed-release pharmaceutical composition prepared by hot-melt extrusion comprises: an extrudate comprising posaconazole, a first enteric polymer and a first non-enteric polymer; and an extra-granular fraction comprising a second enteric polymer and a second non-enteric polymer, wherein the first enteric polymer and second enteric polymer are each independently selected from the group consisting of a hydroxypropylmethyl cellulose, a polyvinylacetate, a polymethacrylic acid, and mixtures thereof; wherein the first non-enteric polymer and second non-enteric polymer are each independently selected from the group consisting of polyvinylpyrrolidone, poly (vinylpyrrolidone/vinylacetate), poly (ethylene oxide/propylene oxide), polyethylene glycol, hydroxypropylmethyl cellulose (hypromellose), hydroxypropyl cellulose, hydroxyethyl cellulose, maltodextrin and mixtures thereof; and wherein the pharmaceutical composition may be administered in the fed or fasted state.

Other embodiments relate to methods for treatment or prevention of a fungal infection, which method comprises administering to a human in a fasted state, a delayed-release pharmaceutical composition, comprising an effective amount of posaconazole or a pharmaceutically acceptable salt thereof; wherein following oral administration of the pharmaceutical compositions, there is no substantial difference in at least one pharmacokinetic parameter selected from the group consisting of $T_{max}$, $C_{max}$, $AUC_{0-t}$ and $AUC_{0-infinity}$ of the azole anti-fungal drug, when comparing administration in the fed state and the fasted state.

Yet another embodiment relates to a process for preparing a solid oral dosage form, comprising: (a) dry-blending a mixture of posaconazole, hydroxypropylmethyl cellulose acetate succinate (HPMC-AS) and hydroxypropyl cellulose (HPC), (b) heating the mixture to a temperature above the glass transition temperature (Tg) of the hydroxypropylmethyl cellulose acetate succinate (HPMC-AS) and the hydroxypropyl cellulose (HPC), thereby forming a molten dispersion of the posaconazole in hydroxypropylmethyl cellulose acetate succinate (HPMC-AS) and hydroxypropyl cellulose (HPC), and (c) cooling the dispersion formed in (b) to provide a composition of posaconazole in hydroxypropylmethyl cellulose acetate succinate (HPMC-AS) and hydroxypropyl cellulose (HPC). In certain aspects, the process can further comprise the steps of: (d) milling the composition from (c) to provide granules comprising posaconazole; and (e) mixing the granules from (d) with an extra-granular mixture comprising one or more excipients selected from the group consisting of hypromellose acetate succinate, hydroxypropyl cellulose, microcrystalline cellulose, croscarmellose sodium and colloidal silicon dioxide, to form a blend. In certain aspects, the process may further comprise the steps of: (f) compressing the blend into tablets or filling the blend into a capsule shell; and (g) optionally coating the tablets or capsule shell.

Each of embodiments above may further have one or more of the following additional elements in any combination:

Element 1: wherein the enteric polymer is selected from the group consisting of hydroxypropylmethyl cellulose, polyvinylacetate, polymethacrylic acid and mixtures thereof;

Element 2: wherein the non-enteric polymer is selected from the group consisting of polyvinylpyrrolidone, poly (vinylpyrrolidone/vinylacetate), poly (ethylene oxide/propylene oxide), polyethylene glycol, hydroxypropylmethyl cellulose (hypromellose), hydroxypropyl cellulose, hydroxyethyl cellulose, maltodextrin and mixtures thereof;

Element 3: wherein the azole anti-fungal drug is posaconazole, or a pharmaceutically acceptable salt thereof.

Element 4: wherein the pharmaceutical composition is in the form of a tablet, a capsule, a caplet, beads or granules.

Element 5: wherein the pharmaceutical composition comprises from about 50 mg to about 400 mg of the azole anti-fungal drug. In certain aspects, it is preferred to provide treatment by administering from about 100 mg of posaconazole to about 300 mg of posaconazole per day, or at least about 100 mg of posaconazole.

Element 6: wherein the enteric polymer is hydroxypropylmethyl cellulose acetate succinate (HPMC-AS).

Element 7: wherein the weight ratio of hydroxypropylmethyl cellulose acetate succinate (HPMC-AS) to azole anti-fungal drug is from 1:1 to 4:1. In certain aspects, the weight ratio of posaconazole to enteric polymer is from 1:1 to 1:8, preferably from 1:2 to 1:5, and more preferably 1:3 to 1:4.

Element 8: wherein the non-enteric polymer is hydroxypropyl cellulose (HPC).

Element 9: wherein the azole anti-fungal drug is molecularly dispersed in a mixture of hydroxypropylmethyl cellulose acetate succinate (HPMC-AS) and hydroxypropyl cellulose (HPC).

Element 10: wherein the enteric polymer is hydroxypropylmethyl cellulose acetate succinate (HPMC-AS) and the non-enteric polymer is hydroxypropyl cellulose (HPC).

Element 11: wherein the pharmaceutical composition retains at least about 95% of the potency of posaconazole after storing the pharmaceutical composition at 40° C. and 75% relative humidity for at least three months.

Element 12: wherein at least one pharmacokinetic parameter, subsequent to administration of the solid oral dosage form in the fasting state, is from 75% to 125% of the pharmacokinetic parameter in the fed state.

Element 13: wherein the area under the serum concentration versus time curve ($AUC_{0-inf}$) of the posaconazole, subsequent to administration of the solid oral dosage form in the fasting state, is from 75% to 125% of the mean area under the posaconazole serum concentration versus time curve ($AUC_{0-inf}$) resulting from administration of the solid oral dosage form in a fed state.

Element 14: wherein the area under the serum concentration versus time curve ($AUC_{0-t}$) of the posaconazole, subsequent to administration of the solid oral dosage form in the fasting state, is from 75% to 125% of the mean area under the posaconazole serum concentration versus time curve (A $AUC_{0-t}$) resulting from administration of the solid oral dosage form in a fed state.

Element 15: wherein the area under the $T_{max}$ of the posaconazole, subsequent to administration of the solid oral dosage form in the fasting state, is from 75% to 125% of the $T_{max}$ resulting from administration of the solid oral dosage form in a fed state.

Element 16: wherein the area under the $C_{max}$ of the posaconazole, subsequent to administration of the solid oral dosage form in the fasting state, is from 75% to 125% of the $C_{max}$ resulting from administration of the solid oral dosage form in a fed state.

By way of non-limiting example, exemplary combinations applicable to the embodiments described in this application may include any combination with one or more of Elements 1-14, described above.

EXAMPLES

The following examples are provided for illustrative purpose only and should not be considered as limiting the scope of present invention in any way.

Comparative Example

TABLE 1

Preparation of Posaconazole delayed release tablets

| S. No. | Name of Material | Unit Qty (mg/tablet) |
|---|---|---|
| Extrudate | | |
| 1 | Posaconazole | 100 |
| 2 | Hypromellose acetate succinate | 325 |
| Extra-granular Inactive Ingredients | | |
| 3 | Hydroxypropyl cellulose | 75 |
| 4 | Microcrystalline cellulose | 59 |
| 5 | Croscarmellose sodium | 25 |
| 6 | Colloidal silicon dioxide | 3 |
| 7 | Magnesium stearate | 3 |
| Coating up to 3% w/w | | |
| 8 | Opadry II Yellow 85F520317 | 17.7 |
| 9 | Water, purfied@ | q. s |
| Total weight of coated tablet (mg) | | 607.7 | q.s. - quantity sufficient

Manufacturing Procedure:

Posaconazole and Hypromellose acetate succinate were weighed in the required quantities as shown in Table 1. The components were sifted and blended in a blender bin. The mixture was then fed to Zone 1 of a hot melt extruder. The hot melt extruder had temperature zones through which a twin screw conveys and kneads the solid and molten material, then finally extrudes molten mass through a die hole attached at the end. The different zones were maintained at different temperatures, such that the material passing through the tunnel path was exposed to ascending temperatures. The last three out of four zones were melting zones, as summarized in Table 2.

TABLE 2

Temperature profile of different zones of hot melt extruder

| Zones of HME | Set Temperature |
|---|---|
| Zone 1 | 30 ± 10° C. |
| Zone 2 | 80 ± 5° C. |
| Zone 3 | 130 ± 5° C. |
| Zone 4 | 130 ± 5° C. |

The 240 mm screw was designed to have suitable set of conveying, shovel and kneading elements. The feed rate and screw rpm were maintained in the range to get about 1.8-3 gm/min of output. The molten extruded strands coming out of die were cooled to solid sheets by passing through a rotating chilled roller and conveyer belt. The chilled sheets were milled using hammer mill to get ASTM #40 mesh passed granules.

Extra-granular hydroxypropyl cellulose, microcrystalline cellulose, croscarmellose sodium and colloidal silicon dioxide were weighed in required quantity. The components are sifted and blended with the chilled milled granules in a blender. Magnesium stearate was weighed in a required quantity as per the unit formula shown in the above table and sifted. The extra-granular blend was mixed with the sifted magnesium stearate in a blender.

The lubricated blend was compressed into tablets using tablet press. Opadry-II was dispersed in water to prepare a dispersion using mechanical stirrer. The compressed tablets were coated with aqueous Opadry dispersion in pan coater.

Example 1

TABLE 3

Preparation of Posaconazole delayed release tablets

| S. No. | Name of Material | Unit Qty (mg/tablet) |
|---|---|---|
| Extrudate | | |
| 1 | Posaconazole | 100 |
| 2 | Hypromellose acetate succinate | 300 |
| 3 | Hydroxypropyl cellulose | 20 |
| Extra-granular Inactive Ingredients | | |
| 4 | Hydroxypropyl cellulose | 55 |
| 5 | Hypromellose acetate succinate | 25 |
| 6 | Microcrystalline cellulose | 59 |
| 7 | Croscarmellose sodium | 25 |
| 8 | Colloidal silicon dioxide | 3 |
| 9 | Magnesium stearate | 3 |
| Coating up to 3% w/w | | |
| 10 | Opadry II Yellow 85F520317 | 17.7 |
| 11 | Water, purified@ | q. s |
| Total weight of coated tablet (mg) | | 607.7 | q.s. - quantity sufficient

Manufacturing Procedure:

Posaconazole, Hypromellose acetate succinate and Hydroxypropyl cellulose were weighed in the required quantities as shown in Table 3. The components were sifted and blended in a blender bin. The mixture was then fed to Zone 1 of a hot melt extruder. The hot melt extruder had temperature zones through which a twin screw conveys and kneads the solid and molten material, then finally extrudes molten mass through a die hole attached at the end. The different zones were maintained at different temperatures, such that the material passing through the tunnel path was exposed to ascending temperatures. The last three out of eight zones were melting zones, as summarized in Table 4.

TABLE 4

Temperature profile of different zones of hot melt extruder

| Zones of HME | Set Temperature |
|---|---|
| Zone 1 | 15 ± 10° C. |
| Zone 2 | 30 ± 10° C. |
| Zone 3 | 45 ± 5° C. |
| Zone 4 | 80 ± 5° C. |

TABLE 4-continued

Temperature profile of different zones of hot melt extruder

| Zones of HME | Set Temperature |
|---|---|
| Zone 5 | 100 ± 5° C. |
| Zone 6 | 130 ± 5° C. |
| Zone 7 | 130 ± 5° C. |
| Zone 8 | 130 ± 5° C. |
| Die Head Temp | 145 ± 10° C. |

The 1205 mm screw was designed to have suitable set of conveying, shovel and kneading elements. The feed rate and screw rpm were maintained in the range to get about 6.8-10.2 kg/hour of output. The molten extruded strands coming out of die were cooled to solid sheets by passing through a rotating chilled roller and conveyer belt. The chilled sheets were milled using hammer mill to get ASTM #40 mesh passed granules.

X-ray powder diffraction pattern of these granules is provided in FIG. 1.

Extra-granular hypromellose acetate succinate, hydroxypropyl cellulose, microcrystalline cellulose, croscarmellose sodium and colloidal silicon dioxide were weighed in required quantity. The components are sifted and blended with the chilled milled granules in a blender. Magnesium stearate was weighed in a required quantity as per the unit formula shown in the above table and sifted. The extra-granular blend was mixed with the sifted magnesium stearate in a blender.

The lubricated blend was compressed into tablets using tablet press. Opadry-II yellow was dispersed in water to prepare a dispersion using mechanical stirrer. The compressed tablets were coated with aqueous Opadry dispersion in pan coater.

Example 2

Dissolution profiles of Posaconazole DR tablets as prepared in example 1, comparative example were compared with commercially available NOXAFIL® DR tablets in 0.01N HCl acid media and followed by pH 6.5 McIlvaine buffer with 0.126% Polysorbate 80.

When tested by using USP apparatus II (paddle); 500 ml of acid medium for 120 minutes and followed by 1000 ml of pH 6.5 McIlvaine buffer with 0.126% Polysorbate 80 for 60 minutes at 37° C. and stirred at 75 RPM, the dissolution profile of Posaconazole DR tablets as prepared in example 1, comparative example and NOXAFIL® DR tablets are provided in the following table 5. Samples were withdrawn at 120 minutes in acid media and 5, 10, 15, 20, 30, 45-& 60-minutes time points in buffer media and analysed using HPLC system with UV detector at a wavelength 232 nm.

TABLE 5

| Media | Time point (min) | % drug released | | |
|---|---|---|---|---|
| | | NOXAFIL® DR Tab | Comparative Example | Example 1 |
| Acid stage: 0.01 N HCl | 120 | 4 | | 4 |
| Buffer stage: pH 6.5 | 5 | 68 | 39 | 27 |
| | 10 | 70 | 66 | 53 |
| | 15 | 53 | 73 | 69 |
| | 20 | 44 | 73 | 77 |
| | 30 | 35 | 59 | 78 |
| | 45 | 30 | 39 | 67 |
| | 60 | 26 | 33 | 47 |

Figure 2:
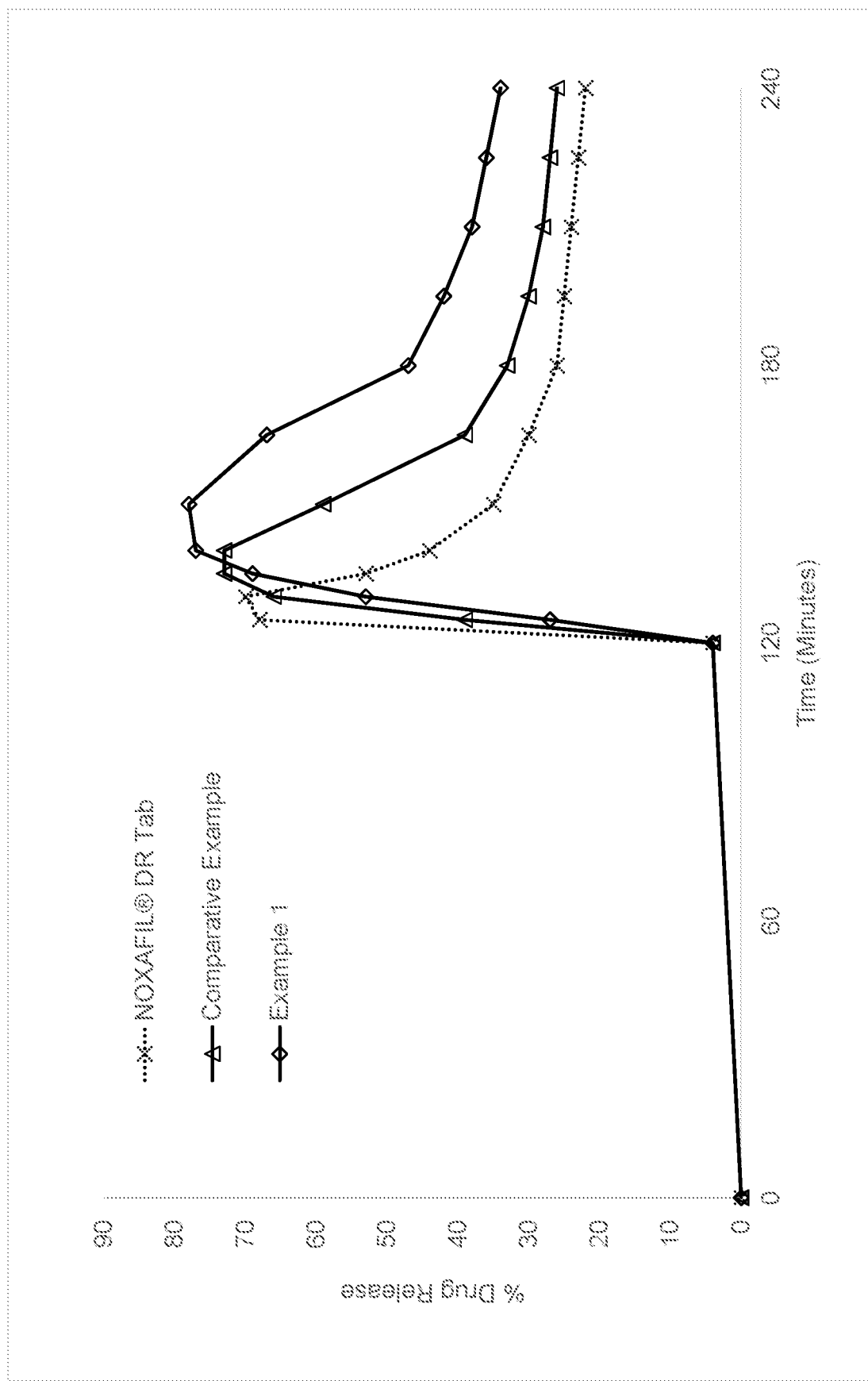
FIG. 2 illustrates a graphical representation of the comparative dissolution profiles in acid stage followed by buffer medium, for NOXAFIL® DR tablets, Posaconazole DR tablets prepared in Example 1 and comparative example 1.

Comparative dissolution profiles of Posaconazole DR tablets as prepared in example 1, comparative example and NOXAFIL® DR tablets in 0.01 N HCl acid media followed by pH 6.5 McIlvaine buffer are illustrated in FIG. 2.

Example 3

Posaconazole DR tablets as prepared in example 1 containing 100 mg of posaconazole were evaluated in two separate pharmacokinetic studies.

Study 1: An open label, balanced, randomized, single-dose, two-treatment, two-sequence, two-period, two-way crossover bioequivalence study of posaconazole delayed-release tablets, 100 mg of example 2 as test product and commercially available NOXAFIL® (Posaconazole delayed-release tablets, 100 mg) as reference product in healthy, adult, human subjects under fasting condition. The subjects were fasted overnight for at least 10.00 hours before schedule time of dosing. Investigational products, allocated as per the randomization schedule, were administered orally at scheduled dosing time with 240±02 mL of dosing water. Sampling schedule was planned to provide an adequate estimation of $C_{max}$ and to cover the plasma concentration-time curve long enough to provide a reliable estimate of the extent of absorption. A two-week washout period between administration of the dose for each of the two treatments was used.

Figure 3:
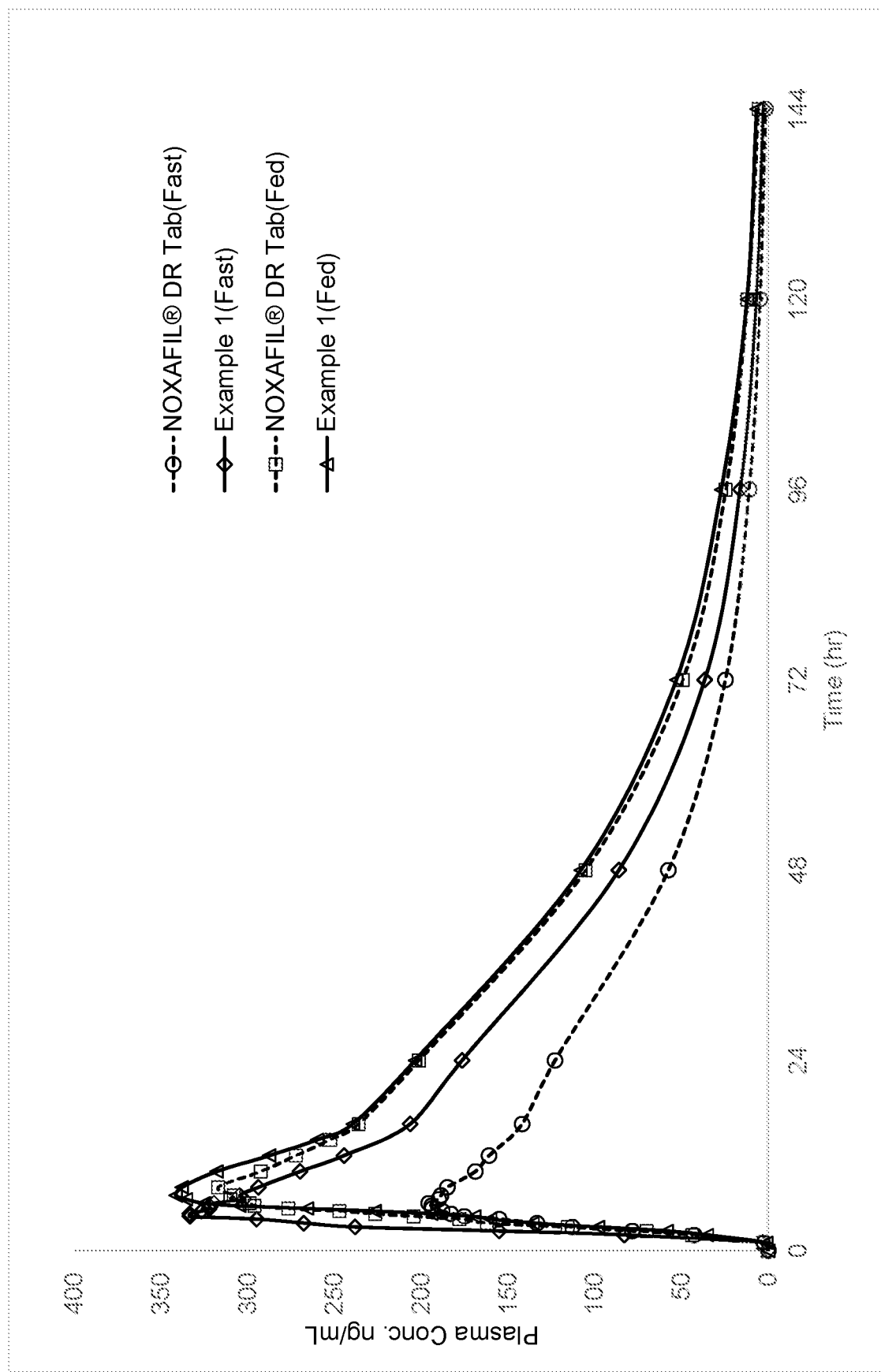
FIG. 3 illustrates a graphical representation of the plasma levels for the NOXAFIL® DR tablets and Posaconazole DR tablets prepared in Example 1, observed under fasting and fed conditions.

Study 2: An open label, balanced, randomized, single-dose, two-treatment, two-sequence, two-period, two-way crossover bioequivalence study of posaconazole delayed-release tablets, 100 mg of example 1 as test product and commercially available NOXAFIL® (Posaconazole delayed-release tablets, 100 mg) as reference product in healthy, adult, human subjects under fed condition. The subjects will be fasted overnight for at least 10.00 hours before schedule time of scheduled time of start of a high-fat, high calorie breakfast. Investigational products, allocated as per the randomization schedule, were administered orally at schedule dosing time exactly 30 minutes after the start of a high-fat high-calories breakfast to each subject and were instructed to swallow it with 240±02 mL of dosing water. Sampling schedule was planned to provide an adequate estimation of $C_{max}$ and to cover the plasma concentration-time curve long enough to provide a reliable estimate of the extent of absorption. A two-week washout period between administration of the dose for each of the two treatments was used. A plot of the mean bloodlevels from the fasted and fed study is shown in the FIG. 3.

TABLE 6

| | Fasting (N = 36) | | | Fed (N = 25) | | |
|---|---|---|---|---|---|---|
| | $C_{max}$ (ng/mL) | $AUC_{0-t}$ (ng.hr/mL) | $AUC_{0-\infty}$ (ng.hr/mL) | $C_{max}$ (ng/mL) | $AUC_{0-t}$ (ng.hr/mL) | $AUC_{0-\infty}$ (ng.hr/mL) |
| NOXAFIL® DR Tablets | 211 | 6858 | 7000 | 372 | 11676 | 11922 |
| Example 1 Tablet | 378 | 10672 | 10801 | 384 | 12087 | 12442 |
| T/R | 178 | 155 | 154 | 103 | 103 | 104 |
| 90% CI | 161-197 | 144-167 | 143-165 | 94-112 | 99-107 | 101-107 |

T/R: test/reference × 100
CI: confidence interval

These results demonstrate that the test formulation provides an improved bioavailability than the reference formulation in fasting state. The results further demonstrate that the test formulation exhibits less variability in pharmacokinetic parameters than the reference formulation and much less variability than oral suspension formulation under fasted conditions.

Variability date for the two commercially available formulations is compared with the pharmaceutical composition of the present invention in the below table.

Mean (% CV) posaconazole pharmacokinetic parameters following single-dose NOXAFIL® oral suspension administration of 200 mg under Fed and Fasted conditions as reported in approved product information leaflet (PIL)

Mean (% CV) posaconazole pharmacokinetics parameters following single oral dose administration of 300 mg NOXAFIL® Delayed-Release Tablet to healthy subjects under Fasting and Fed conditions as reported in approved PIL Mean (% CV) posaconazole pharmacokinetics parameters following single oral dose administration of 100 mg Posaconazole Delayed-Release Tablet as prepared in example 1 to healthy subjects under Fasting and Fed conditions

TABLE 7

| | Mean Values (% CV); Single oral dose | | | |
| --- | --- | --- | --- | --- |
| | Fasting | | Fed | |
| Description | Mean $C_{max}$ (ng/mL) | AUC (ng·hr/mL) | Mean $C_{max}$ (ng/mL) | AUC (ng·hr/mL) |
| NOXAFIL ® Oral suspension | 132 (50) | 4179 (31) | 512 (34) | 15059 (26) |
| NOXAFIL ® DR Tablet | 935 (34) | 26200 (28) | 1060 (25) | 38400 (18) |
| Example 1 Tablet | 386.92 (21.2) | 10907.95 (21.7) | 396.58 (25.3) | 12666.92 (20.9) |

% CV: Coefficient of variation

Having now fully described this invention, it will be understood by those of ordinary skill in the art that it can be performed within a wide equivalent range of parameters without affecting the scope of the invention or any embodiment thereof. All publications, patent applications and patents disclosed herein are incorporated by reference in their entirety.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

While compositions and methods are described herein in terms of "comprising" various components or steps, the compositions and methods can also "consist essentially of" or "consist of" the various components and steps.

The invention claimed is:

1. A delayed-release pharmaceutical composition, comprising:
   a. an intra-granular material comprising posaconazole, or a pharmaceutically acceptable salt thereof, which is molecularly dispersed in a mixture of hydroxypropylmethyl cellulose acetate succinate (HPMC-AS) and hydroxypropyl cellulose (HPC); and
   b. an extra-granular material comprising a blend of an enteric polymer and a non-enteric polymer;
   wherein the extra-granular material comprises an enteric polymer selected from the group consisting of hydroxypropylmethyl cellulose acetate succinate, hydroxypropylmethyl cellulose phthalate, polyvinylacetate phthalate and mixtures thereof;
   wherein the extra-granular material comprises a non-enteric polymer selected from the group consisting of polyvinylpyrrolidone, polyethylene glycol, hydroxypropylmethyl cellulose, hydroxypropyl cellulose, hydroxyethyl cellulose and mixtures thereof; and
   wherein the pharmaceutical composition may be administered to a patient without regard to food.

2. The pharmaceutical composition according to claim 1, wherein the pharmaceutical composition is in the form of a tablet, a capsule, a caplet, beads or granules.

3. The pharmaceutical composition according to claim 1, wherein the pharmaceutical composition comprises from about 50 mg to about 400 mg of the posaconazole, or pharmaceutically acceptable salt thereof.

4. The delayed release composition according to claim 1, wherein the enteric polymer in the extra-granular material comprises hydroxypropylmethyl cellulose acetate succinate (HPMC-AS).

5. The delayed release composition according to claim 1, wherein the weight ratio in the intra-granular material of hydroxypropylmethyl cellulose acetate succinate (HPMC-AS) to the posaconazole, or a pharmaceutically acceptable salt thereof is from 1:1 to 4:1.

6. The delayed release composition according to claim 1, wherein the non-enteric polymer in the extra-granular material is hydroxypropyl cellulose (HPC).

7. A delayed-release pharmaceutical composition prepared by hot-melt extrusion comprising:
   a. an extrudate comprising posaconazole or a pharmaceutically acceptable salt thereof, a first enteric polymer and a first non-enteric polymer; and
   b. an extra-granular fraction comprising a blend of a second enteric polymer and a second non-enteric polymer,
   wherein the first enteric polymer and second enteric polymer are each independently selected from the group consisting of hydroxypropylmethyl cellulose acetate succinate, hydroxypropylmethyl cellulose phthalate, polyvinylacetate phthalate and mixtures thereof;
   wherein the first non-enteric polymer and second non-enteric polymer are each independently selected from the group consisting of polyvinylpyrrolidone, polyethylene glycol, hydroxypropylmethyl cellulose, hydroxypropyl cellulose, hydroxyethyl cellulose, and mixtures thereof; and
   wherein the pharmaceutical composition may be administered to a patient without regard to food.

8. The delayed release composition according to claim 7, wherein the pharmaceutical composition is in the form of a tablet, a capsule, a caplet, beads or granules.

9. The delayed release composition according to claim 7, wherein the pharmaceutical composition comprises from about 50 mg to about 400 mg posaconazole, or a pharmaceutically acceptable salt thereof.

10. The delayed release composition according to claim 7, wherein at least one of the first enteric polymer or the second enteric polymer is hydroxypropylmethyl cellulose acetate succinate (HPMC-AS).

11. The delayed release composition according to claim 7, wherein at least one of the first non-enteric polymer or the second non-enteric polymer is hydroxypropyl cellulose (HPC).

12. The delayed release composition according to claim 7, wherein the first enteric polymer is hydroxypropylmethyl cellulose acetate succinate (HPMC-AS) and the first non-enteric polymer is hydroxypropyl cellulose (HPC).

13. The delayed release composition according to claim 12, wherein the weight ratio of hydroxypropylmethyl cellulose acetate succinate to posaconazole is from 1:1 to 4:1.

14. The delayed release composition of claim 7, wherein the pharmaceutical composition retains at least about 95% of the potency of posaconazole after storing the pharmaceutical composition at 40° C. and 75% relative humidity for at least three months.

15. A method for treatment or prevention of a fungal infection, which method comprises administering to a human a delayed-release pharmaceutical composition of claim 7, comprising an effective amount of posaconazole or a pharmaceutically acceptable salt thereof;
wherein following oral administration of the pharmaceutical composition in the fasted state, there is no substantial difference in at least one pharmacokinetic parameter selected from the group consisting of $T_{max}$, $C_{max}$, $AUC_{0-t}$ and $AUC_{0-infinity}$ of the posaconazole, or a pharmaceutically acceptable salt thereof, as compared to the at least one pharmacokinetic parameter after oral administration in the fed state.

16. The method of claim 15, wherein at least one pharmacokinetic parameter, subsequent to administration of the solid oral dosage form in the fasting state, is from 75% to 125% of the pharmacokinetic parameter in the fed state.

17. The method of claim 15, wherein the area under the serum concentration versus time curve ($AUC_{0-inf}$) of the posaconazole or a pharmaceutically acceptable salt thereof, subsequent to administration of the solid oral dosage form, is from 75% to 125% of the mean area under the posaconazole serum concentration versus time curve ($AUC_{0-inf}$) resulting from administration of the solid oral dosage form in a fed state.

18. A process for preparing a solid oral dosage form, comprising:
   a. dry-blending posaconazole, hydroxypropylmethyl cellulose acetate succinate (HPMC-AS) and hydroxypropyl cellulose (HPC) to form a mixture,
   b. heating the mixture to a temperature above the glass transition temperature ($T_g$) of the hydroxypropylmethyl cellulose acetate succinate (HPMC-AS) and the hydroxypropyl cellulose (HPC), thereby forming a molten dispersion of the posaconazole in hydroxypropylmethyl cellulose acetate succinate (HPMC-AS) and hydroxypropyl cellulose (HPC); and
   c. cooling the dispersion formed in (b) to provide a composition of posaconazole in hydroxypropylmethyl cellulose acetate succinate (HPMC-AS) and hydroxypropyl cellulose (HPC),
   d. milling the composition from (c) to provide granules comprising posaconazole; and
   e. mixing the granules from (d) with an extra-granular mixture comprising an enteric polymer and a non-enteric polymer to form a blend,
   wherein the enteric polymer is selected from the group consisting of hydroxypropylmethyl cellulose acetate succinate, hydroxypropylmethyl cellulose phthalate, polyvinylacetate phthalate and mixtures thereof; and
   wherein the non-enteric polymer is selected from the group consisting of polyvinylpyrrolidone, polyethylene glycol, hydroxypropylmethyl cellulose, hydroxypropyl cellulose, hydroxyethyl cellulose and mixtures thereof.

19. The process of claim 18, further comprising the steps of:
   f. compressing the blend into tablets or filling the blend into a capsule shell; and
   g. optionally, coating the tablets or capsule shell.

* * * * *